Sept. 12, 1961 E. S. BOERNER Plant Pat. 2,090
ROSE PLANT
Filed Nov. 15, 1960
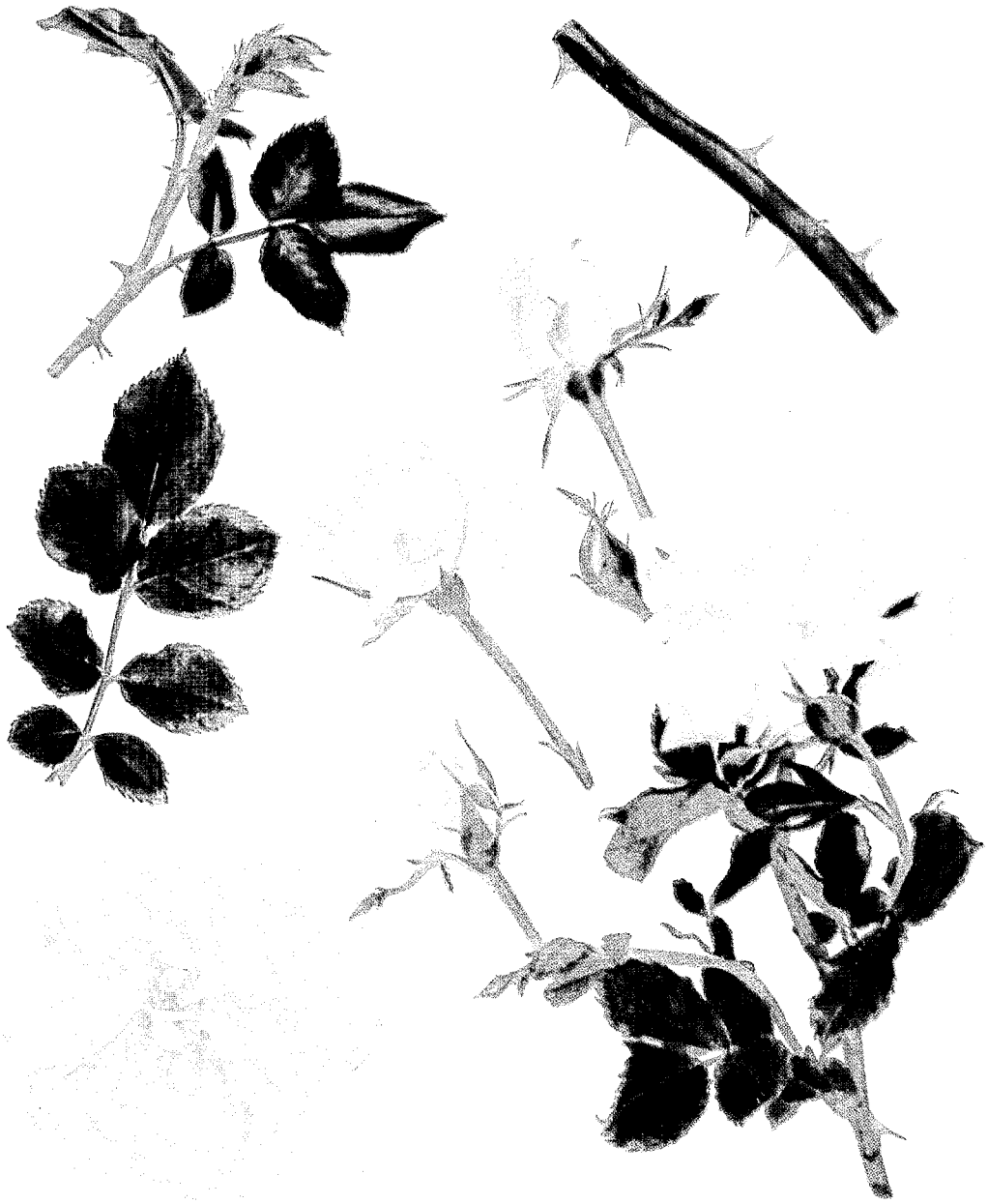
Inventor.
E. S. Boerner
By: Robb & Robb
Attorneys.

United States Patent Office

Plant Pat. 2,090
Patented Sept. 12, 1961

2,090
ROSE PLANT

Eugene S. Boerner, Newark, N.Y., assignor to Jackson & Perkins Company, Newark, N.Y., a corporation of New York Filed Nov. 15, 1960, Ser. No. 69,532
1 Claim. (Cl. 47—61)

The present invention relates to a new and distinct variety of rose plant of the floribunda class, which was originated by me by crossing the variety named "Gold Cup" (Plant Patent No. 1,683) with the variety named "Pigmy Gold" (Plant Patent No. 1,114).

The primary objective of this breeding was to produce a new rose of medium size which would be attractive and desirable as a general garden variety, as well as suitable for hedging. This objective was fully achieved, along with other desirable improvements, as evidenced by the following unique combination of characteristics which are outstanding in the new variety and which distinguish it from its parents, as well as from all other varieties of which I am aware:

(1) A medium tall habit of growth;
(2) Leathery and glossy foliage;
(3) A free flowering habit;
(4) Quick repetition of bloom; and
(5) A distinctive and uniform Empire Yellow general color tonality of the flowers throughout the life thereof.

Asexual reproduction of my new variety by budding, as performed at Newark, New York, and also at Pleasanton, California, shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.
*Seed parent.*—"Gold Cup."
*Pollen parent.*—"Pigmy Gold."
Classification:
*Botanic.*—Floribunda.
*Commercial.*—Floribunda.

*Flower*

(Observations made from specimens grown outdoors at Newark, New York, in the late afternoon during the latter part of the month of August.)

Blooming habit: Recurrent—free-flowering and quick-repeating.
Bud:
*Size.*—Medium.
*Form.*—Ovoid; is not affected by wet or hot weather.
*Color.*—When sepals first divide—Chartreuse Yellow, Plate 31. When petals begin to unfurl—Empire Yellow, Plate 4, with lower half of petals lightly overcast with Deep Chrome, Plate 3. When half-blown: inside of petals—Pinard Yellow, Plate 4, overcast with Apricot Yellow, Plate 4; reverse of petals—Empire Yellow, Plate 4, lightly overcast with Pinard Yellow, Plate 4.
*Sepals.*—Branched and with "hood" above bud; curl back when petals begin to unfurl. Color: inside—Turtle Green, Plate 32; outside—Oil Green, Plate 5.
*Calyx.*—Color—Oil Green, Plate 5. Shape—funnel.

Size—slender. Aspect—smooth. Odor when rubbed—none.
*Peduncle.*—Length—medium. Aspect — smooth. Strength—erect; slender. Color—Yellowish Oil Green, Plate 5.
*Opening.*—Opens up well; is not affected by adverse weather conditions.
Bloom:
*Size.*—Medium. Average size when fully expanded—from 3½ inches to 4 inches.
*Borne.*—Both singly and several together.
*Stems.*—Medium length; normal strength.
*Form (when first open).*—From cupped to full. Permanence—retains its form to the end, but outer petals curl back.
*Petalage.*—Double (full but open center). Number of petals under normal conditions—50.
*Color.*—Center of flower—Empire Yellow, Plate 4, lightly overcast with Apricot Yellow, Plate 4. Outer petals—Pinard Yellow, Plate 4, with lower half of petals lightly overcast with Empire Yellow, Plate 4. Base of petals (aiglet)—Lemon Chrome, Plate 4. Inside of petals—Pinard Yellow, Plate 4, lightly overcast with Empire Yellow, Plate 4. Reverse of petals—Pale Lemon Yellow, Plate 4, lightly overcast with Pinard Yellow, Plate 4. General tonality from a distance—Empire Yellow, Plate 4.
*Discoloration.*—General tonality at end of first day—Empire Yellow, Plate 4, lightly overcast with Apricot Yellow, Plate 4. Second day—Empire Yellow, Plate 4. Third day—Empire Yellow, Plate 4.
Petals:
*Texture.*—Leathery; is not affected by wet or hot weather.
*Appearance.*—Inside—satiny. Outside—shiny.
*Form.*—Oval.
*Arrangement.*—Informal (with "rags" in center).
*Petaloids in center.*—Few; small.
*Persistence.*—Drop off cleanly.
*Fragrance.*—Moderate. Nature—tea (average hybrid tea scent).
*Lasting quality.*—On the plant—long. As cut flower—long.

*Genital organs*

Stamens, anthers: Medium size; many; regularly arranged around styles. Color—Light Cadmium, Plate 4.
Stamens, filaments (threads): Medium length. Color—Empire Yellow, Plate 4.
Pollen: Color—Maize Yellow, Plate 4.
Styles: Loosely separated; uneven length; medium length; thin.
Stigmas: Color—Pale Lemon Yellow, Plate 4.
Ovaries: All enclosed in calyx.
Hips: None.
Seeds: None.

*Plant*

Form: Bush.
Growth: Vigorous; medium tall; branching.
Foliage: Compound of 3–7 leaflets.
*Size.*—Medium.
*Quantity.*—Abundant.
*Color.*—New foliage: upper side—Deep Dull Yellow-Green, Plate 32, with serrations Van Dyke Red, Plate 13; under side—Chromium Green, Plate 32, with serrations Van Dyke Red, Plate 13. Old foliage: upper side—Dark Cress Green, Plate 31; under side—Cress Green, Plate 31.
*Shape.*—Oval pointed.

*Texture.*—Upper side—leathery; glossy. Under side—smooth.

*Ribs and veins.*—Ordinary.

*Edge.*—Serrated (saw-toothed).

*Serration.*—Single; small.

*Leaf stem.*—*Color*—Light Cress Green, Plate 31. Under side—prickly.

*Stipules.*—Short; smooth.

Wood:

*New wood.*—Color — Lettuce Green, Plate 5. Bark—smooth.

*Old wood.*—Color — Varley's Green, Plate 5. Bark—smooth.

Thorns:

*Thorns.*—Quantity: on main stalks from base—ordinary; on laterals from stalk—ordinary. Form—narrow base; medium length; straight. Color (when young) — Eugenia Red, Plate 13. Position—irregular.

*Prickles.*—Quantity: on main stalks—none; on laterals none.

*Short needles.*—Quantity: on main stalks—none; on laterals—none.

I claim:

A new and distinct variety of rose plant of the floribunda class, substantially as herein shown and described, characterized particularly as to novelty by the unique combination of a medium tall habit of growth, leathery and glossy foliage, a free-flowing habit, quick repetition of bloom, and a distinctive and uniform Empire Yellow general color tonality of the flowers throughout their life.

No references cited.